United States Patent
Johnson et al.

(10) Patent No.: US 8,532,349 B2
(45) Date of Patent: Sep. 10, 2013

(54) ENCAPSULATED IMAGE ACQUISITION DEVICES HAVING ON-BOARD DATA STORAGE, AND SYSTEMS, KITS, AND METHODS THEREFOR

(75) Inventors: Gregory E. Johnson, Boulder, CO (US); Edward R. Dowski, Jr., Lafayette, CO (US)

(73) Assignee: Omnivision Technologies, Inc., Santa Clara, CA (US)

( * ) Notice: Subject to any disclaimer, the term of this patent is extended or adjusted under 35 U.S.C. 154(b) by 892 days.

(21) Appl. No.: 12/698,783

(22) Filed: Feb. 2, 2010

(65) Prior Publication Data

US 2011/0187843 A1     Aug. 4, 2011

(51) Int. Cl.
*G06K 9/00*     (2006.01)

(52) U.S. Cl.
USPC ......................................................... 382/128

(58) Field of Classification Search
USPC ..... 382/128–134; 128/920–925; 356/39–49; 600/407–414, 424–426; 345/581–618
See application file for complete search history.

(56) References Cited

U.S. PATENT DOCUMENTS

| 2007/0232851 A1 | 10/2007 | Fujimori et al. |
| 2007/0244359 A1 | 10/2007 | Cabiri et al. |
| 2008/0021270 A1 | 1/2008 | Suzushima et al. |
| 2008/0255409 A1 | 10/2008 | Graumann et al. |

FOREIGN PATENT DOCUMENTS

| CN | 1561902 | 1/2005 |
| CN | 1976621 A | 8/2005 |
| CN | 2726521 | 9/2005 |
| CN | 101365986 | 2/2009 |
| CN | 100473329 | 4/2009 |
| EP | 1709901 | 10/2006 |
| WO | WO-2007/051147 | 5/2007 |
| WO | WO 2007/051147 | 5/2007 |
| WO | WO 2007/076198 | 7/2007 |

OTHER PUBLICATIONS

"PCT European Search Report for Application No. 10196618.2-2319.", 6 pages.
European Search Report dated May 19, 2011 (EP patent application No. 10196618), 3 pgs.
Wikipedia, "Pap Test" http://en.wikipedia.org/wiki/Pap_test, Apr. 30, 2010, pp. 1-9.
Craig Medical. "Landmark PSA Prostate Cancer Screening Test" http://www.craigmedical.com/psa4_home.htm , Jan. 14, 2010, 2 pgs.
D. Fleischer, "Capsule endoscopy: The voyage is fantastic—will it change what we do?", Gastrointestinal Endoscopy, vol. 56, No. 3, 2002, pp. 452-456.

*Primary Examiner* — Atiba O Fitzpatrick
(74) *Attorney, Agent, or Firm* — Blakely Sokoloff Taylor & Zafman LLP

(57) ABSTRACT

A method of one aspect may include receiving an encapsulated image acquisition device having an internal memory. The internal memory may store images acquired by the encapsulated image acquisition device. The images may be transferred from the internal memory to an external memory that is external to the encapsulated image acquisition device. An image analysis station may be selected from among a plurality of image analysis stations to analyze the images. The images may be analyzed with the selected image analysis station. Other methods, systems, and kits are also disclosed.

53 Claims, 11 Drawing Sheets

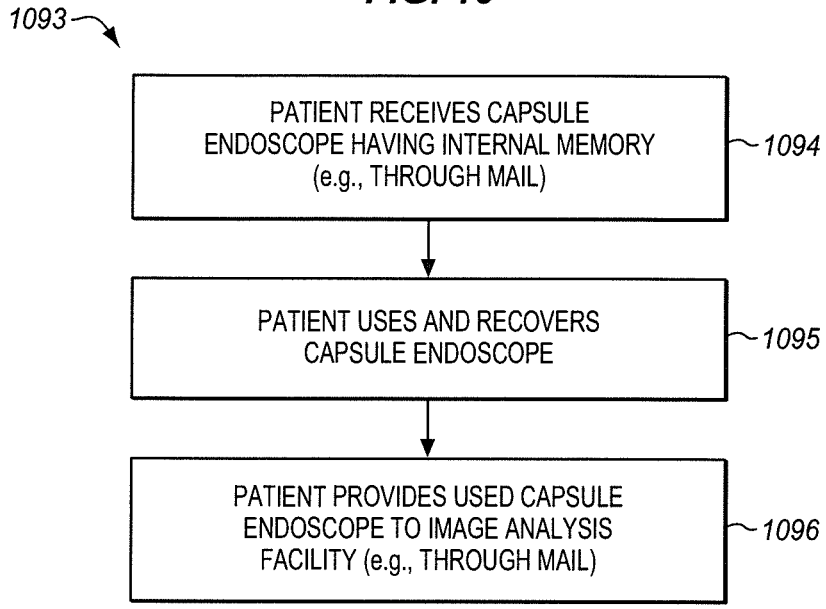
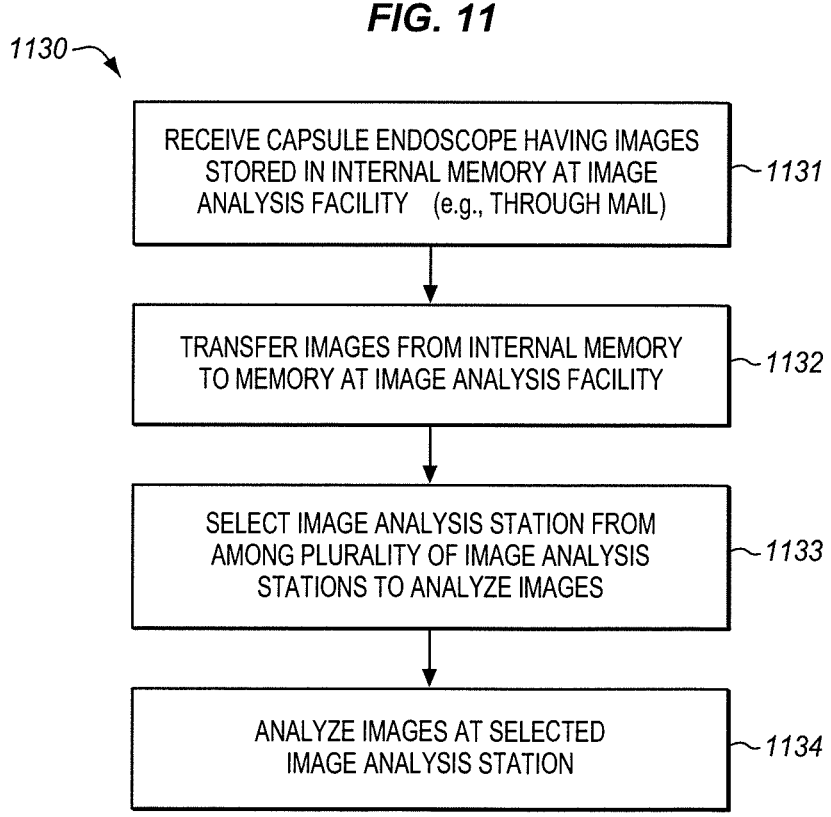

ENCAPSULATED IMAGE ACQUISITION DEVICES HAVING ON-BOARD DATA STORAGE, AND SYSTEMS, KITS, AND METHODS THEREFOR

BACKGROUND

1. Field

Embodiments relate to encapsulated image acquisition devices. In particular, embodiments relate to encapsulated image acquisition devices having on-board data storage.

2. Background Information

Image acquisition devices have been used to inspect or observe conduits. For example, the image acquisition devices may move through the conduits and obtain images of the inside of the conduits. Typically, the number of images obtained may be quite large. Analysis of the images, due to the typically large number of images that need to be analyzed, may tend to be time consuming, expensive, and/or inconvenient. There would be significant advantages to ways of reducing the time, expense, and/or inconvenience of analyzing the images.

BRIEF DESCRIPTION OF THE SEVERAL VIEWS OF THE DRAWINGS

The invention may best be understood by referring to the following description and accompanying drawings that are used to illustrate embodiments of the invention. In the drawings:

FIG. 10 is a block flow diagram of an example embodiment of a method that a patient may perform.

FIG. 11 is a block flow diagram of an example embodiment of a method that an image analysis facility may perform.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

Figure 1:
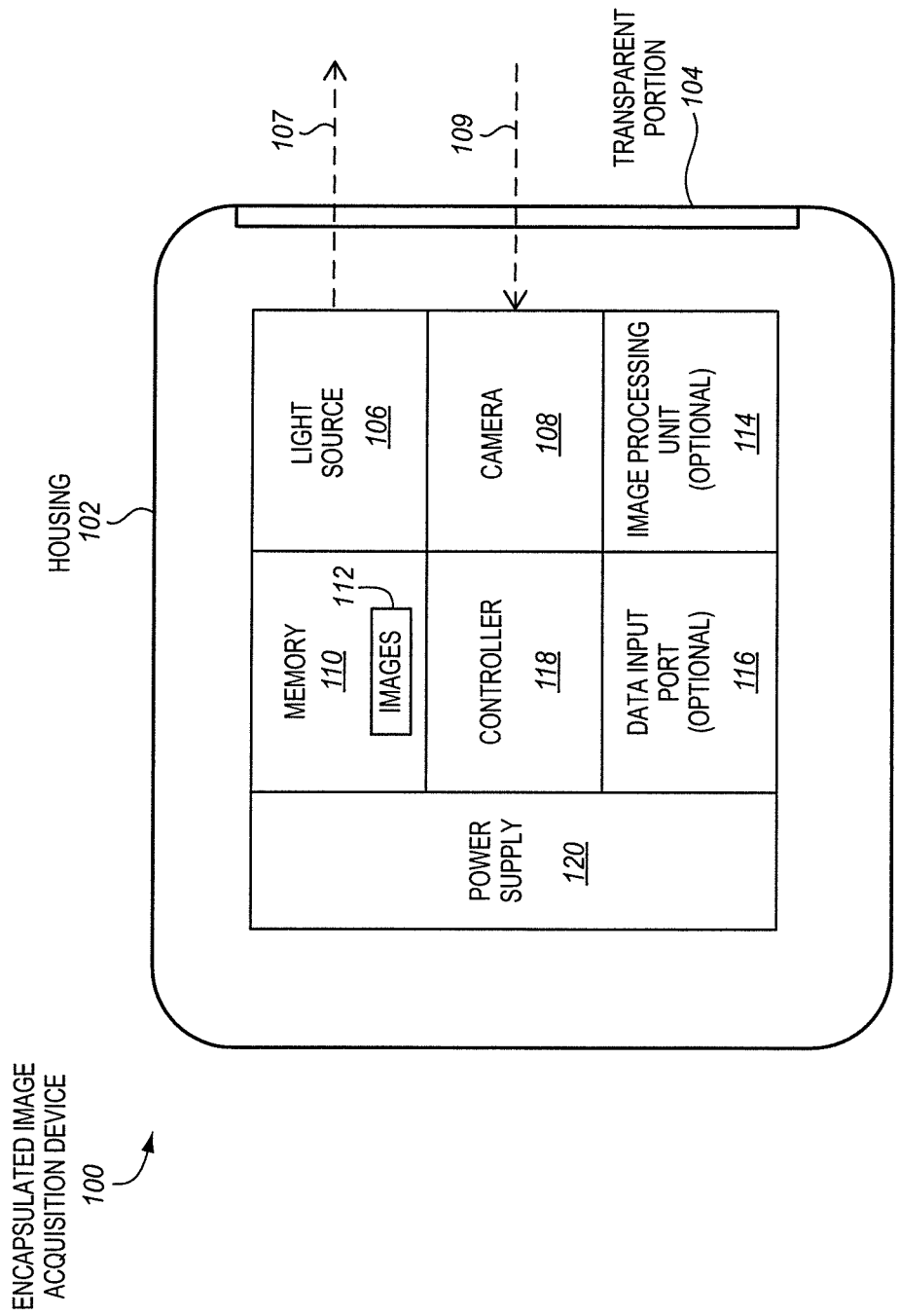
FIG. 1 is a block diagram of an example embodiment of an encapsulated image acquisition device.

FIG. 1 is a block diagram of an example embodiment of an encapsulated image acquisition device 100.

The encapsulated image acquisition device has a housing 102. The housing encapsulates the image acquisition device and may in some cases provide a hermetic seal to the components located within the housing. Various different shapes of the housing are suitable, such as, for example, cubes, elongated cubic shapes, capsules, spheres, and sphereoidal shapes, to name just a few examples.

The housing has at least one transparent portion 104. The transparent portion is transparent to light that is to be passed through the transparent portion. In the illustrated embodiment, the transparent portion comprises a transparent side, or portion of a side, of the housing. If desired, one or more other sides or portions (e.g., an opposite side or portion thereof) may also optionally be transparent and used for image acquisition.

The encapsulated image acquisition device has a light source 106 enclosed within the housing. The light source is operable to transmit light 107 through the transparent portion of the housing. The light source may include at least one light, or a plurality of lights. Examples of suitable types of lights include, but are not limited to, semiconductor lights, various different types of light emitting diodes (LEDs), lasers (e.g., vertical-cavity surface-emitting lasers (VCSELs)), various different types of light bulbs, etc. Visible, ultraviolet, and infrared wavelengths are contemplated. In one or more embodiments, a wavelength of the light source may be varied during inspection, for example to allow features to be better imaged or analyzed.

The encapsulated image acquisition device has a camera 108 enclosed within the housing. As used herein, the camera is to be interpreted broadly as a device capable of acquiring an image. The camera is operable to acquire images of surfaces. By way of example, the camera may detect light 109, which may represent at least some of the light 107 from the light source that has been reflected or backscattered from a surface.

The encapsulated image acquisition device has a memory 110 enclosed within the housing. The memory is operable to store images 112 obtained by the camera and optionally other data. In one or more embodiments, the memory may include a non-volatile memory that is capable of retaining the images or data even when power is not provided to the non-volatile memory. Specific examples of suitable types of non-volatile memory include, but are not limited to, flash (e.g., NAND flash), various types of read-only memory (ROM), and magnetoresistive RAM (MRAM), to name just a few examples. In various embodiments, the encapsulated image acquisition device may have at least 16 Gb of memory, at least 32 Gb of memory, at least 64 Gb of memory, at least 128 Gb of memory, or more. This amount of memory allows a large number of images to be stored.

In one or more embodiments, the encapsulated image acquisition device may optionally have an image processing unit 114. In one aspect, the image processing unit may include image compression circuitry to compress the images obtained by the camera. Advantageously, this may allow more images to be stored in a given amount of memory. Other types of circuitry that may optionally be included in the image processing unit includes, but is not limited to, image improvement processing circuitry, encryption circuitry, etc. Alternatively, the image processing unit may optionally be omitted.

The encapsulated image acquisition device may optionally have a data output port 116. The data output port is operable to output the images 112 and optionally other data stored in the memory. For example, the data output port may include a port that may be coupled with a probe or other electrical conductor to read images and data from the memory. Alternatively, the data output port may optionally be omitted. For example, the device may represent a disposable or one-time-use device that may be broken or dissembled to recover the memory 110.

The encapsulated image acquisition device also has a controller 118 and a power supply 120. The controller may control various different types of operations performed by the image acquisition device. The power supply may provide power to the image acquisition device. By way of example, the power supply may include a battery.

In one or more embodiments, an encapsulated image acquisition device, such as, for example, the encapsulated image acquisition device shown in FIG. 1, may be used as an inspection and/or observation device. The encapsulated image acquisition device may potentially be used to obtain images of otherwise difficult to view surfaces or features for purposes of inspection and/or observation. In one or more embodiments, the encapsulated image acquisition device may be used as a conduit inspection and/or observation device to obtain images of otherwise difficult to view surfaces or features within a conduit.

Figure 2:
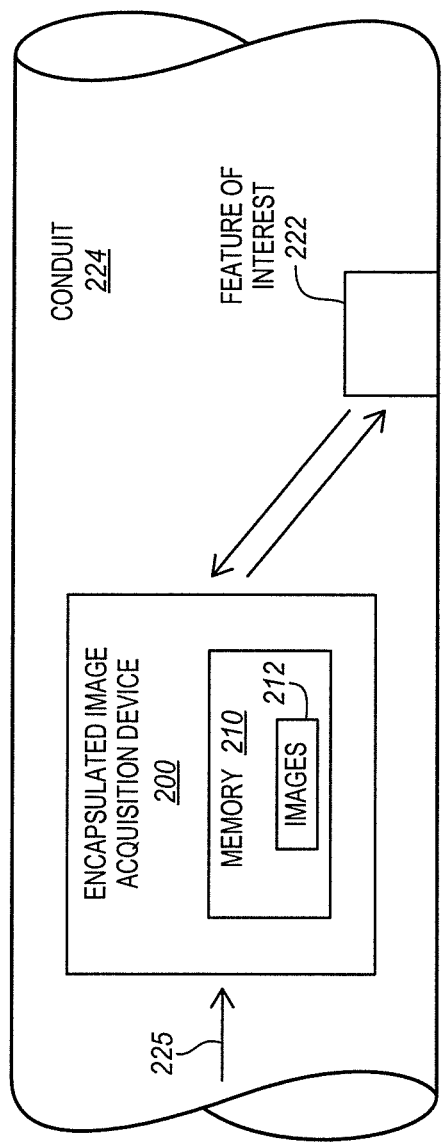
FIG. 2 illustrates an embodiment of an encapsulated image acquisition device obtaining an image of a feature of interest within a conduit.

FIG. 2 illustrates an embodiment of an encapsulated image acquisition device 200 obtaining an image of a feature of interest 222 within a conduit 224. The conduit may represent a channel or passageway, generally one in which material may be conveyed.

In one or more embodiments, the conduit may represent a man-manufactured (man-made) conduit. Examples of suitable types of man-made conduits include, but are not limited to, pipes, pipelines, tubes, ducts, and long hollow cylinders, to name just a few examples. Alternatively, in one or more embodiments, the conduit may represent a natural or anatomical conduit. Examples of suitable types of natural or anatomical conduits include, but are not limited to, tubular organs, bodily tubes, body lumens, elongated cavities, tracts, digestive tracts, intestines, bowels, colons, esophagus, and stomachs, to name just a few examples.

The encapsulated image acquisition device is located within the conduit. The encapsulated image acquisition device may move through the conduit in the direction of arrow 225. As the encapsulated image acquisition device moves through the conduit, the encapsulated image acquisition device may autonomously obtain and store images 212 in an internal memory 210 thereof. In one or more embodiments, the encapsulated image acquisition device may autonomously obtain and store a sequence of images of the inner surface of the conduit as the encapsulated image acquisition device moves through the conduit.

Images may be obtained of much, most, or all of the inner surface of the conduit, or of a particular section or portion of the conduit of interest. Often, from hundreds, to thousands, or even tens of thousands of images, or more, may be obtained and stored in the on-board memory. As previously mentioned, data compression may optionally be used to reduce the size of the images that are stored. The images may be color images, black and white images, or a combination thereof. Images based on non-visible spectrum light (e.g., infrared, ultraviolet, etc.) are also contemplated.

Referring again to the illustration, the encapsulated image acquisition device is shown obtaining an image of the feature of interest 222 on an inner surface of the conduit. The feature of interest represents a feature that is of interest to the inspection or observation of the conduit. Various different types of features of interest are contemplated for the variety of different uses of the encapsulated image acquisition device. To further illustrate certain concepts, a few examples of different uses of the encapsulated image acquisition device will be discussed in detail.

As one example, in one or more embodiments, the encapsulated image acquisition device may be used as a so-called "pig" to inspect a manufactured ("man-made") conduit. For example, the encapsulated image acquisition device may be introduced into the man-made conduit at an entry point (e.g., a so-called "pig launcher"), the encapsulated image acquisition device (the so-called "pig") may be moved or move down the conduit, and then the encapsulated image acquisition device may be removed or recovered from the conduit at a exit point (e.g., a so-called "pig catcher"). Examples of suitable types of man-made conduits for which the encapsulated image acquisition device may be used include, but are not limited to, industrial pipelines, industrial pipes, industrial tubes, industrial plumbing, residential plumbing, and residential tubing, to name just a few examples. Particular examples include, but are not limited to, pipelines and pipes used to convey oil, gas, water, and sewer, piping at chemical plants and refineries, tubes within heat exchangers, plumbing systems in homes and buildings, sprinkler systems, etc. A few Examples of possible features of interest for such inspection or observation include, but are not limited to, cracks, damage, holes, leaks, corrosion, constrictions, blockages, clogs, fouling, deposits, and buildup, to name just a few examples.

As another example, in one or more embodiments, the encapsulated image acquisition device may be used as an endoscope to inspect a bodily conduit. For example, the encapsulated image acquisition device may be an image acquisition device that may be swallowed, used to image some or all of the digestive tract, and then excreted and recovered. Examples of suitable conduits that may be imaged by the image acquisition device include, but are not limited to, the esophagus, the stomach, the duodenum, and the intestines (e.g., the duodenum, the jejunum, the ileum, the cecum, the colon, and the rectum), and other parts of the digestive tract. Examples of possible features of interest for such inspection or observation include, but are not limited to, discolorations, protuberances, bleeding, signs of cancer or other disease, other abnormalities, and other diagnostic features.

As yet another example, in one or more embodiments, the encapsulated image acquisition device may be used to acquire images of a man-made or bodily conduit for educational purposes. For example, to educate students about what the inside of the conduit looks like.

These are just a few illustrative examples. Other examples are contemplated and will be apparent to those skilled in the art and having the benefit of the present disclosure.

Analyzing images obtained by an encapsulated image acquisition device to detect or identify features of interest for inspection, observation, or other purposes may tend to be time consuming. This is particularly true when large numbers of images are analyzed and/or when the analysis of individual images is time consuming. In addition, the cost of analyzing the images may tend to be high when highly paid specialized professionals are used to analyze the images. For example, paying an engineer to analyze thousands of images of a pipe, pipeline, or other man-made conduit may tend to be expensive. Likewise, it may tend to be expensive to pay a physician, or like degreed medical specialist, to analyze thousands of images of a bodily conduit. In addition, the engineer's or physician's time may be limited and better spent elsewhere.

In one or more embodiments, rather than an engineer, physician, or user of the encapsulated image acquisition device analyzing the images, the encapsulated image acquisition device may be mailed or otherwise transferred to an image analysis facility to have the images analyzed. Advantageously, this may help to reduce the cost of the analysis, help to allow the engineer's, physician's, or user's time to be spent elsewhere, and/or help to reduce the inconvenience on the engineer, physician, or user.

Figure 3:
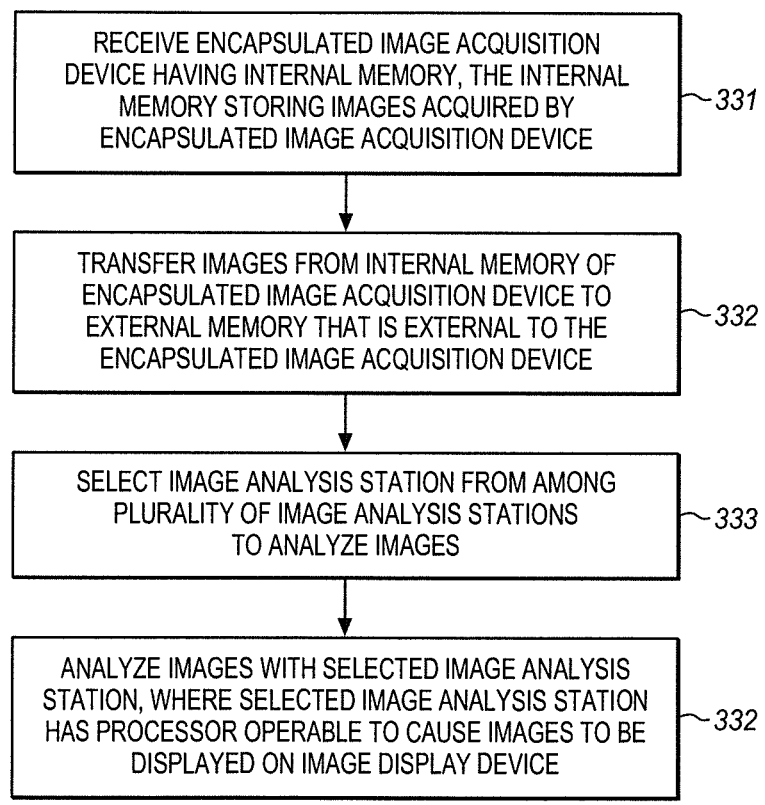
FIG. 3 is a block flow diagram of an example embodiment of a method of analyzing images that may be performed by an image analysis facility.

FIG. 3 is a block flow diagram of an example embodiment of a method 330 of analyzing images that may be performed by an image analysis facility. An encapsulated image acquisition device having an internal memory storing images acquired by the encapsulated image acquisition device may be received at the image analysis facility, at block 331. In one or more embodiments, the used encapsulated image acquisition device may be mailed to the image analysis facility by a person who used the encapsulated image acquisition device to acquire the images.

The images may be transferred from the internal memory of the encapsulated image acquisition device to an external memory or storage that is external to the encapsulated image acquisition device, at block 332. The external memory or storage may potentially be used to store images from a plurality of, or a large number of, different image acquisition devices. If the images are compressed or encrypted, then decompression and decryption may be performed.

In one or more embodiments, an automated encapsulated image acquisition device handling and data recovery system may be used to at least semi-autonomously handle (e.g., move, and/or hold, and/or orient) and/or at least semi-autonomously recover the images from the device. The automated handling and data recovery system may include special-purpose equipment or machines. Examples of possible special-purpose equipment or machines to handle the encapsulated image acquisition devices includes, but is not limited to, conveyors, robotic devices, and image acquisition device handling, holding, and/or orienting equipment, to name just a few examples. Examples of special-purpose equipment or machines to transfer the images includes, but is not limited to, robotic devices, machine vision equipped robotic machines, electrical probes, data output port detection devices, and other encapsulated image acquisition device handling, holding, and/or orienting equipment, to name just a few examples.

Referring again to the illustration, an image analysis station may be selected from among a plurality of image analysis stations to analyze the images, at block 333. The number of image analysis stations appropriate for a particular facility will generally depend upon various factors, such as the number of images analyzed by the facility, the amount of time needed to analyze the images, the number of customers who use the facility to have their images analyzed, etc. By way of example, in implementations where relatively few images are to be analyzed, one, two, three, or four image analysis stations, for example, may be sufficient or appropriate. In other implementations where relatively more images are to be analyzed, at least five, at least ten, at least 20, or more image analysis stations may be appropriate. This number may vary depending upon the region in which the facility is located, and may be relatively lower initially and increase over time as increasingly more customers use the facility for analysis. In one or more embodiments, each of the image analysis stations may have a processor and an image display device. Each processor may be operable to cause images to be displayed on the corresponding image display device. In one or more embodiments, each image analysis station may optionally have specialized image display and/or analysis logic (e.g., hardware, software, or a combination). In one or more embodiments, the image analysis stations may represent specialized workstations or computer systems that are adapted to perform image analysis.

The images may be analyzed with the selected image analysis station, at block 334. The images to be analyzed, which have previously been stored in the external memory or storage, may either be transferred to the selected image analysis station, or accessed by the selected image analysis station. A processor of the selected image analysis station may cause the images to be displayed on a display screen, monitor, or other image display device. Recall that in one or more embodiments the encapsulated image acquisition device may acquire a sequence of images of an inner surface of a conduit as the devices moves through the conduit. In such a case, the images may be displayed one by one often in the sequence that they were obtained. The image analysis station may have a keyboard, mouse, cursor control device, joystick, or other user input device, which may allow a user to manually interact with the station, for example, to scroll through images and/or input results of the analysis. In one or more embodiments, at least hundreds, or at least thousands, or even tens of thousands of images, or more, may be analyzed.

As previously mentioned, in one or more embodiments, the analysis of the images may be used to detect or identify features of interest in the images, if they exist. Examples of possible features of interest in pipes, pipelines, and other man-made conduits include, but are not limited to, cracks, damage, holes, leaks, corrosion, constrictions, blockages, clogs, fouling, deposits, and buildup, to name just a few examples. Examples of possible features of interest in organs of the digestive tract and other bodily conduits include, but are not limited to, discolorations, protuberances, bleeding, signs of cancer or other disease, other abnormalities, and other diagnostic features.

In one or more embodiments, a technician may analyze the images displayed on the display device. In one or more embodiments, the technician may not be a physician, engineer, or other highly trained and highly paid professional. Rather, in one or more embodiments, the technician (at least the average or typical technician) may be an individual with less than three years of college education and/or without a college degree, at least in the subject matter to which the analysis pertains. The technician may nevertheless specialize in, and have suitable training in, analyzing images to detect particular features of interest in the images. By way of example, depending upon the type of analysis, a suitable amount of training may range from several weeks to several months, or perhaps a year, of formal training. The hourly wages of the technician may be significantly less than those of an engineer or physician. Advantageously, using technicians to analyze the images, as opposed to engineers or physicians, for example, may help to reduce the overall cost of the analysis.

Although not shown, in one or more embodiments, a report may optionally be generated based on the analysis of the images. The report may be physical or electronic, such as, for example, a printed report, a faxed report, a report communicated electronically (e.g., by email), a computer generated phone call, or some other type of report. In one or more embodiments, the report may indicate whether or not a feature of interest was detected during the analysis. In one or more embodiments, if one or more features of interest were detected, then a report that indicates that the features of interest were detected may be generated. Optionally, physical copies of the images having the features of interest may be generated and provided to the customer along with the report. The physical copies may include color prints or color photographs. Alternatively, electronic copies of the images may be provided, for example by email.

A particular example embodiment method has been shown and described. In this method, numerous specific details have been set forth in order to provide a thorough understanding of certain inventive aspects. This method of disclosure, however, is not to be interpreted as reflecting an intention that all of these details are required in combination. Rather, inventive aspects lie in different portions of the disclosed method. Accordingly, the scope of the invention is not limited to the particular method described above.

Figure 4:
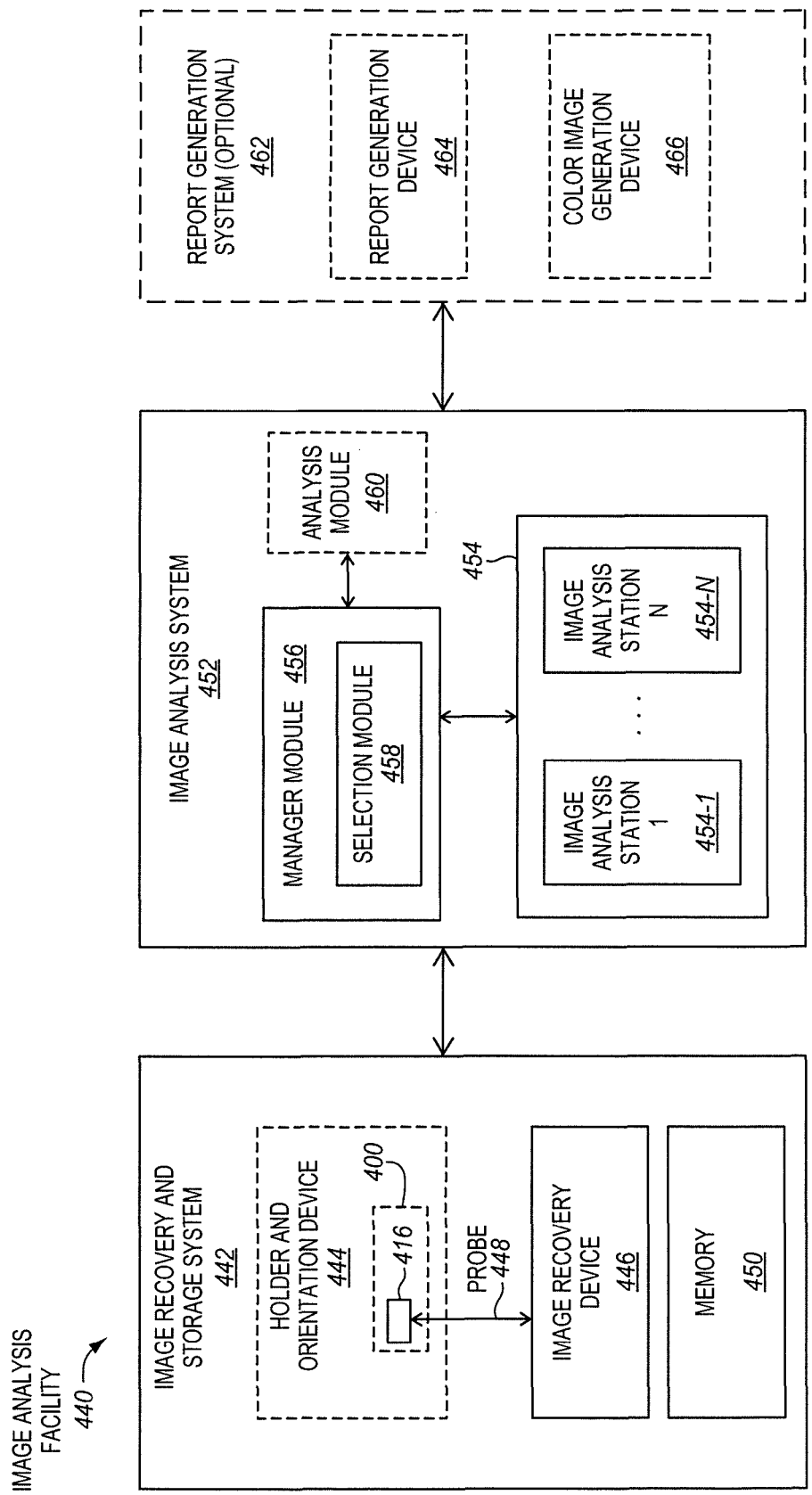
FIG. 4 is a block diagram of an example embodiment of an image analysis facility.

FIG. 4 is a block diagram of an example embodiment of an image analysis facility 440. In one or more embodiments, the image analysis facility may be a special-purpose image analysis facility that specializes in analyzing images to detect particular types of features of interest. As one example, the special-purpose image analysis facility may specialize in analyzing images of pipes, pipelines, or other man-made conduits for particular types of features of interest associated with such conduits. As another example, the special-purpose image analysis facility may specialize in analyzing images of a bodily tract for particular types of features of interest associated with such bodily tracts. The image analysis facility may potentially be a central or regional facility shared by customers in a large region (e.g., several or many states or provinces). In one or more embodiments, the image analysis facility is not a patient receiving physician's office, hospital, or clinic.

The image analysis facility includes an image recovery and storage system 442. The image recovery and storage system may recover images that are stored in an internal memory of an encapsulated image acquisition device 400.

In one or more embodiments, the image recovery and storage system may optionally have an automated encapsulated image acquisition device handling and data recovery system that may be used to at least semi-autonomously handle (e.g., move, and/or hold, and/or orient) and/or at least semi-autonomously recover the images from the device. The automated handling and data recovery system may include special-purpose equipment or machines. Examples of possible special-purpose equipment or machines to handle the encapsulated image acquisition devices includes, but is not limited to, conveyors, robotic devices, and image acquisition device handling, holding, and/or orienting equipment, to name just a few examples. Examples of special-purpose equipment or machines to transfer the images includes, but is not limited to, robotic devices, machine vision equipped robotic machines, electrical probes, data output port detection devices, and other encapsulated image acquisition device handling, holding, and/or orienting equipment, to name just a few examples.

Referring again to the illustration, in the illustrated example embodiment, the image recovery and storage system optionally has an encapsulated image acquisition device holder and orientation device 444. The holder and orientation device may hold the encapsulated image acquisition device and orient the encapsulated image acquisition device relative to an image recovery device 446. For example, in one aspect, the holder and orientation device may orient a data output port 416 of the encapsulated image acquisition device relative to a probe or other conductor 448 of the image recovery device. The probe or other conductor of the image recovery device may then be contacted or coupled with the data output port to recover the images or other data stored in the internal memory of the image acquisition device. In one or more embodiments, the probe or other conductor may optionally be robotically moved to the port. The image recovery device is electrically or otherwise coupled with a memory or storage 450. The recovered images may be stored in the memory or storage. Examples of suitable types of memory or storage include, but are not limited to, servers, hard disks, disk arrays, and other types of mass storage.

The image analysis facility also includes an image analysis system 452 to analyze the recovered images. The image analysis system is coupled with, or otherwise in communication with, the image recovery and storage system to access and/or receive the recovered images now stored in the memory or storage 450. In the description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other. For example, they may be electrically or communicatively coupled through other components, links, a network, etc.

The image analysis system includes at least one, or a plurality of image analysis stations 454. In the illustration a first image analysis station 454-1 and an Nth image analysis station 454-N are shown, where N is an integer. N is at least two, often is at least 5, and in some cases may be at least 10, at least 15, or more. In one or more embodiments, each of the image analysis stations may have a processor and an image display device. Each processor may be operable to cause images to be displayed on the corresponding image display device. In one or more embodiments, each image analysis station may optionally have specialized image display and/or analysis logic (e.g., hardware, software, or a combination). In one or more embodiments, the image analysis stations may represent specialized workstations or computer systems that are adapted to perform image analysis. In one or more embodiments, each station may have a corresponding technician that may manually interact with the station to scroll through images, input results of analysis, etc.

The image analysis system also includes a manager module 456. The manager module is coupled with, or otherwise in communication with, the plurality of image analysis stations. The manager module may perform one or more management functions associated with the plurality of image analysis stations. A few examples of suitable management functions include, but are not limited to, selecting one or more image analysis stations to analyze images, balancing workloads of the image analysis stations, managing redundant image analysis, tracking analysis errors, performing quality control functions associated with the image analysis, and combinations thereof. The manager module may be implemented in hardware (e.g., a circuit or device), software (e.g., instructions or routines), or a combination of hardware and software.

The manager module has an optional selection module 458. The selection module may select at least one image analysis station from among the plurality to analyze a set of images (e.g., a set of images recovered from the encapsulated image acquisition device). This selection may be performed based on various factors, such as, for example, present workload of an image analysis station, a workload quota of an image analysis station, or various other workload distribution or balancing factors. The selection module may be implemented in hardware, software, or a combination of hardware and software.

In one or more embodiments, the image analysis system may optionally have an analysis module 460. The analysis module may include analysis logic such as hardware, software, or a combination of hardware and software. In one or more embodiments, the analysis module may analyze images to detect features of interest. Examples of suitable types of analysis logic include, but are not limited to, pattern recognition logic, pattern matching logic, feature analysis logic, and logic to detect groups of pixels of similar color, to name just a few examples. The analysis module may perform the analysis largely or completely autonomously without human involvement. The analysis module may analyze images instead of, or in addition to, an image analysis station analyzing the images. In one or more embodiments, the analysis of large numbers of images in an image analysis facility may allow an analysis module to "learn" how to better analyze images over time (e.g., by becoming better at identifying features or interest). Optionally, large numbers of features of interest may be used to train or calibrate the analysis module. Optionally, results of error tracking and/or results of redundant analysis may be input to the analysis module in order to improve or better train the analysis module.

The image analysis facility may optionally include a report generation system 462. The report generation system is coupled with, or otherwise in communication with, the image analysis system. The report generation system may generate a report based on the analysis of the images by the image analysis system. The report may indicate whether or not a feature of interest was detected during the analysis. The report may be provided to a customer.

The report may be physical or electronic, such as, for example, a printed report, a faxed report, a report communicated electronically, an emailed report, a computer generated phone call, or some other type of report. The illustrated report generation system optionally includes a report generation device 464. Examples of suitable report generation devices include, but are not limited to, printers, fax machines, Internet connection equipped devices to send emails, and automated phone dialer and message systems, to name just a few examples.

Optionally, physical copies of the images having the features of interest may be generated and provided to the customer along with the report. The physical copies may include color prints or color photographs. The report generation system optionally includes an image generation device 466, such as, for example, a color printer or photograph printing machine, to generate a physical color image. Alternatively, electronic copies of the images may be provided, for example by email.

In one aspect, the image analysis facility may recover and analyze large numbers of images from also large numbers of encapsulated image acquisition devices. This may help to distribute equipment, infrastructure, technician expertise, and other costs associated with the analysis across a greater number of customers, thereby reducing the overall cost of the analysis.

Figure 5:
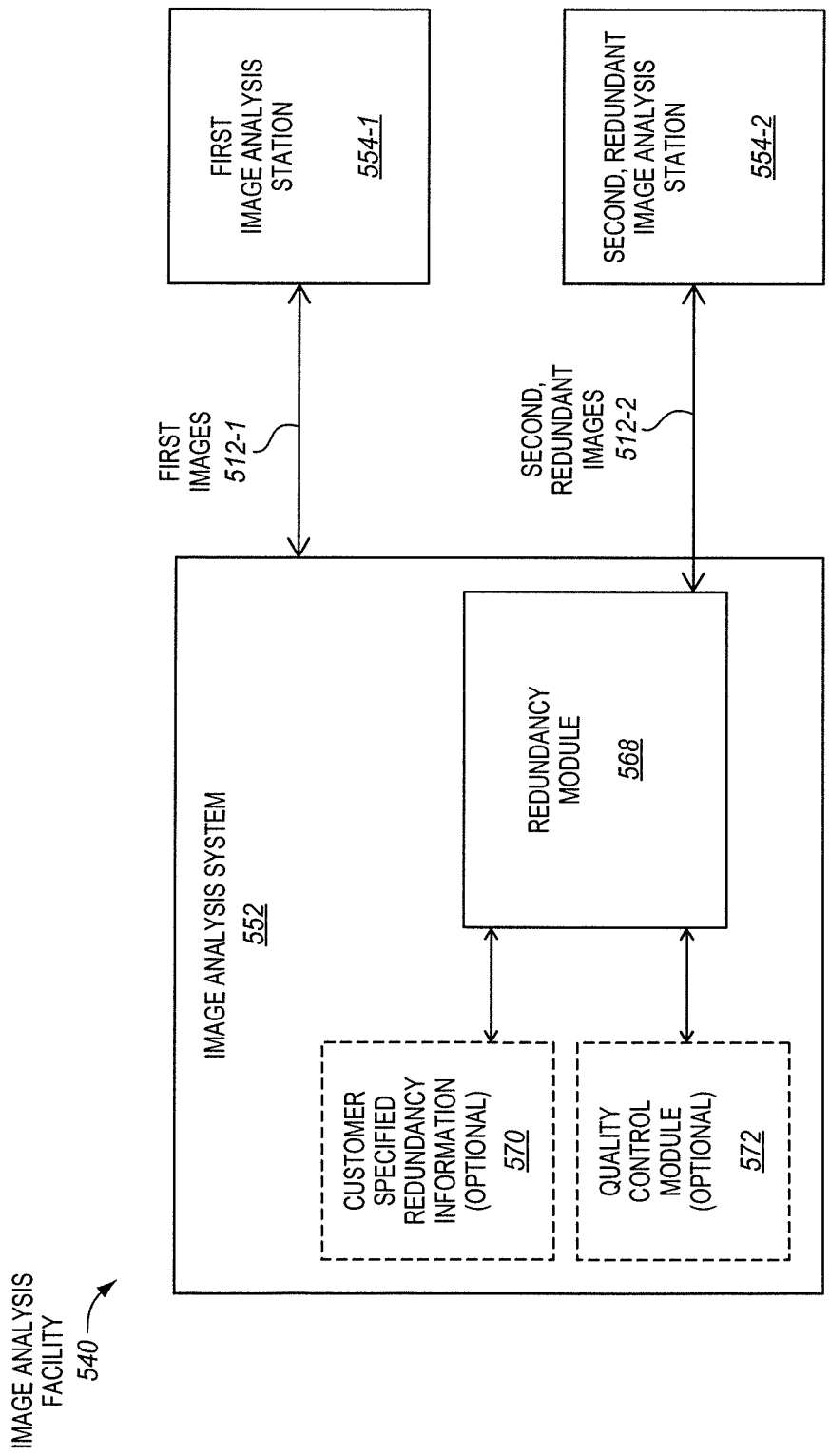
FIG. 5 is a block diagram of an image analysis facility having an example embodiment of a redundancy module.

FIG. 5 is a block diagram of an image analysis facility 540 having an example embodiment of a redundancy module 568 to implement redundant image analysis.

The analysis facility includes an image analysis system 552 having the redundancy module 568. The redundancy manager module may be implemented in hardware, software, or a combination of hardware and software.

The redundancy module may cause at least one image analysis station to redundantly analyze a same set of images also analyzed by at least one other image analysis station. The image analysis system may provide a first set of images 512-1 to a first image analysis station 554-1. In one or more embodiments, the redundancy module may provide, or cause or result in the image analysis system providing, a second, redundant set of images 512-2 to a second, different, redundant image analysis station 554-2. The second, redundant set of images includes at least some images that are identical to images in the first set of images. In one aspect, the entire second, redundant set of images is identical to the first set of images.

The first image analysis station may provide results of the analysis of the first set of images to the image analysis system Likewise, the second, redundant image analysis station may provide results of the analysis of the second, redundant set of images to the image analysis system or the redundancy module.

The image analysis system and/or the redundancy module may compare the results received from the first image analysis station with those received from the second, redundant image analysis station. Discrepancies in the results may be further investigated. For example, if only one of the image analysis stations detected a feature of interest in an image analyzed by both image analysis stations, then that image may be analyzed one or more times by one or more potentially different or independent image analysis stations. In some cases, a senior technician or professional may review the discrepancies. Performing such redundant data analysis may tend to be more costly, but may tend to provide a higher quality of analysis and/or improved likelihood of detecting features of interest when present.

The redundancy may be initiated in different ways. As one example, in one or more embodiments, customer specified redundancy information 570 may optionally be provided to the redundancy module. The customer specified redundancy information may specify that redundant analysis is to be performed on at least some or all of the images. In some cases, three or more independent redundant analysis may be specified. In some cases, the customer specified redundancy information may be stored in the internal memory of the encapsulated image acquisition device. For example, this information may be stored in the memory by a manufacturer of the encapsulated image acquisition device and the customer may purchase or obtain an encapsulated image acquisition device with a desired amount of redundancy.

As another example, in one or more embodiments, an optional quality control module 572 of the image analysis system may optionally provide information specifying redundancy to the redundancy module. For example, if errors or quality control monitored by the quality control module are higher than appropriate, then redundancy may be increased.

Other aspects of the image analysis facility may optionally be similar to, or the same as, those discussed above in conjunction with FIG. 4.

Figure 6:
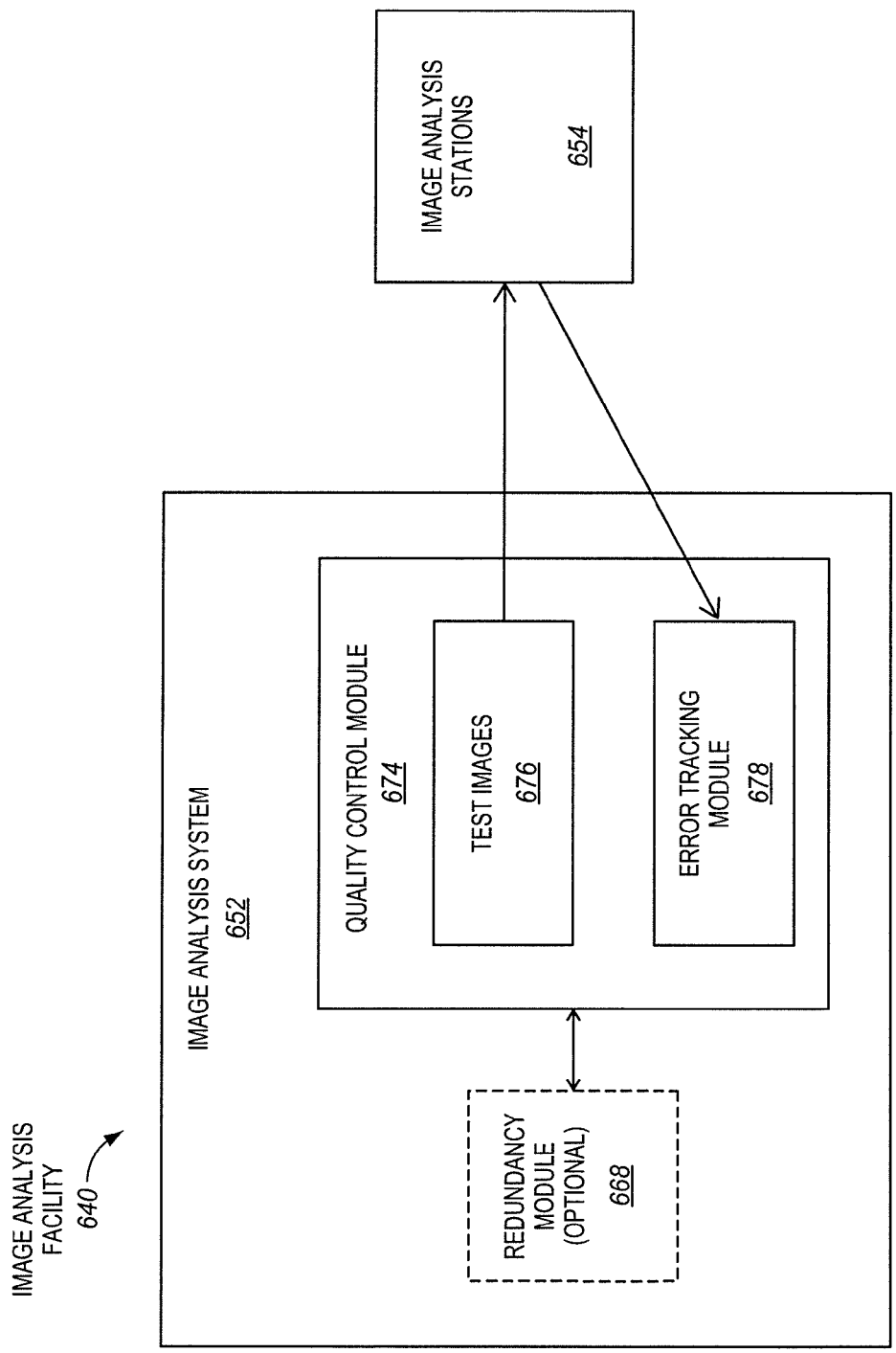
FIG. 6 is a block diagram of an image analysis facility having an example embodiment of a quality control module.

FIG. 6 is a block diagram of an image analysis facility 640 having an example embodiment of a quality control module 674 to perform quality control functions.

The analysis facility includes an image analysis system 652 having the quality control module 674. The quality control module may be implemented in hardware, software, or a combination of hardware and software.

The quality control module includes test images or sets of images 676 having known or well-established analysis results (e.g., analysis results confirmed by thorough analysis or multiple consistent analysis). The test images may include some images that are known to have features of interest, as well as other images that are known not to have features of interest.

The image analysis system and/or the quality control module may provide the test images to one or more of the image analysis stations 654 for analysis of the test images. Actual analysis results of the test images may be provided from the one or more of the image analysis stations back to the image analysis system and/or the quality control module. The quality control module includes an error tracking module 678 to determine and track errors between actual analysis results and expected analysis results for the test images. Discrepancies between the results may be regarded as errors on the part of the image analysis station. Overall errors for all of the image analysis stations as well as individual errors for particular image analysis stations or technicians may optionally be tracked.

The image analysis system may optionally include a redundancy module 668 coupled with or otherwise in communication with the quality control module. The quality control module may optionally provide quality control and/or error information to the redundancy module as previously described. Moreover, the redundancy module may optionally provide information about errors or discrepancies detected during redundant analysis to the quality control module.

Other aspects of the image analysis facility may optionally be similar to, or the same as, those discussed above in conjunction with FIG. 4.

In one or more embodiments, an encapsulated image acquisition device or encapsulated image acquisition device kit may be mailed to a customer or person who is to use the encapsulated image acquisition device. By way of example, the customer or user may request the encapsulated image acquisition device or kit thereof from an image analysis facility, or from an image acquisition device or kit distributor.

Figure 7:
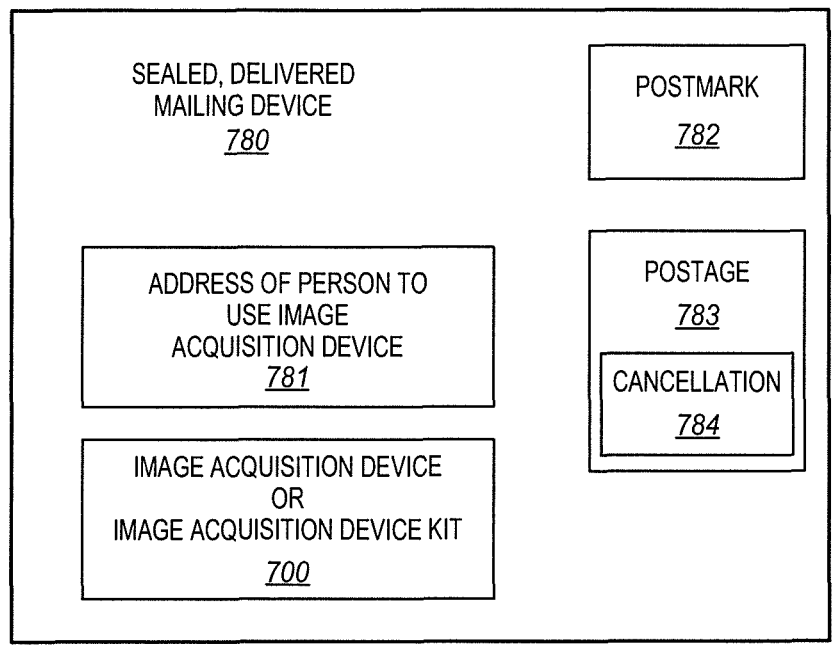
FIG. 7 is a block diagram of an example embodiment of a sealed, delivered mailing device having an image acquisition device or image acquisition device kit sealed therein.

FIG. 7 is a block diagram of an example embodiment of a sealed, delivered mailing envelope, package, or other mailing device 780 having an image acquisition device or image acquisition device kit 700 sealed therein. The mailing device is to be interpreted broadly as any of a wide variety of different envelopes, packages, boxes, or other containers suitable for mailing or distribution by a common carrier.

In one or more embodiments, one or more materials or devices may optionally be included to help protect the image acquisition device. For example, in one or more embodiments, the mailing device may optionally have a conductive foil lining, or other static shielding material, to help protect the image acquisition device from static. Alternatively, a separate pouch or other container having a conductive foil lining, or other static shielding material, may optionally be included to contain and protect the image acquisition device from static.

As shown, in one or more embodiments, the mailing device may have an address 781 of a customer and/or a person who is to use the image acquisition device. For example, the address may be an address of the person's home, residence, or place of work. The address may be located on an exterior of the mailing device at a location predetermined to correspond to the addressee.

As shown, in one or more embodiments, the mailing device may have a postmark 782 on an outer surface thereof. The postmark is to be interpreted broadly to include any text, symbol, graphic, or other mark, applied either by hand or machine, which is used by a post office, other common carrier, or other entity to indicate that the mailing device has been received and/or processed and/or delivered. As one example, the U.S. Postal Service may affix a postmark to the envelope or package, or a stamp thereof, to indicate that the envelope or package and its contents have been received into the care of the U.S. Postal Service. In some cases, the postmark may indicate one or more of a post office, a date, and a time that the envelope or package was received.

As shown, in one or more embodiments, the mailing device may have postage 783 on an outer surface thereof having a cancellation 784. The cancellation is to be interpreted broadly to include any text, symbol, graphic, or other mark, applied either by hand or machine, which is used by a post office, other common carrier, or other entity to indicate that the postage has been used or cancelled. By way of example, the cancellation may include one or more lines, wavy lines, or other marks on or through the postage.

Figure 8:
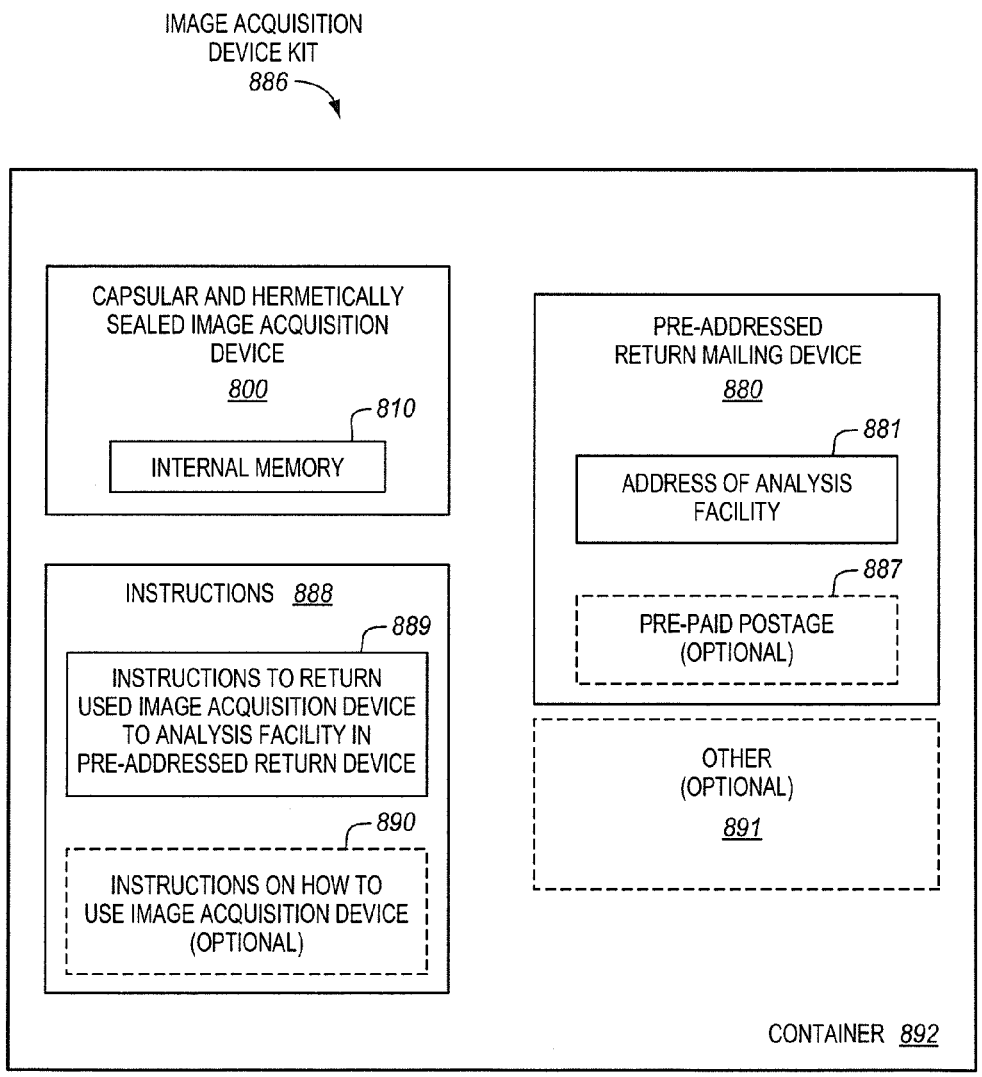
FIG. 8 is a block diagram of an example embodiment of an image acquisition device kit.

FIG. 8 is a block diagram of an example embodiment of an image acquisition device kit 886. As previously mentioned, the kit may be mailed to a customer, or alternatively the kit may be bought in a store.

The kit includes a capsular or encapsulated and generally hermetically sealed image acquisition device 800 having internal memory 810. The internal memory is capable of storing images acquired by the image acquisition device.

The kit also includes a pre-addressed return envelope, package, or other mailing device 880. The mailing device is to be interpreted broadly as any of a wide variety of different envelopes, packages, boxes, or other containers suitable for mailing or distribution by a common carrier. The pre-addressed return mailing device is pre-addressed with an address 881 of an image analysis facility. The image analysis facility is to analyze images obtained by the image acquisition device, which are stored on the memory following use, such as to determine whether or not features of interest are present in the images. In one or more embodiments, the mailing device may also optionally have pre-paid postage 887.

In one or more embodiments, the mailing device 880 may optionally have a conductive foil lining, or other static shielding material, to help protect a used image acquisition device therein from static. Alternatively, the kit may optionally include a separate pouch, wrapper, sleeve, box, envelope, or other container, having a conductive foil, other conductor, or other static shielding material, into which the image acquisition device may be introduced, prior to being introduced into the mailing device, in order to help protect the image acquisition device from static. In one or more embodiments, the mailing device 880 may optionally having padding or cushioning to help mechanically protect the image acquisition device therein. As yet another option, a separate image acquisition device protection device, for example a specialized casing, may optionally be included in the kit.

The kit also includes instructions 888. As shown, in one or more embodiments, the instructions may include a first set of instructions 889 to return the used image acquisition device to the image analysis facility in the pre-addressed return mailing device. As further shown, in one or more embodiments, the instructions may also optionally include a second set of instructions 890 to on how to use the image acquisition device. For example, the second set of instructions may include instructions to introduce the image acquisition device into one end of a conduit, so that the image acquisition device can acquire images of an inner surface of the conduit, and to recover the image acquisition device from another end of the conduit. By way of example, the second set of instructions may explain to that the intended user is to swallow and later recover the image acquisition device when it is excreted. The instructions may include instructions written on paper (e.g., a book, manual, pamphlet, etc.), may include instructions stored on a compact disc (CD), cassette tape, or other machine-readable medium, or a combination thereof. The instructions may include text, figures, drawings, sketches, images, videos, sounds, and the like, and combinations thereof.

In one or more embodiments, one or more other optional components 891 may optionally be included in the kit. A few representative examples of other components that may optionally be included in the kit include, but are not limited to, a protective container or device to protect the image acquisition device during mailing, gloves to protect the user from contents of the conduit, a liability waiver form waiving liability of the image analysis facility in the event of errors in analysis of the images, a redundant analysis request form, etc.

Generally the kit may be included within a container 892. Examples of suitable containers include, but are not limited to, boxes, envelopes, packages, bags, pouches, cans, and other rigid or flexible containers known in the arts. Often, the kit may be sealed within the container, for example sealed within a manufacturer's sealed container.

An example embodiment of a method of using the kit may include a customer or intended user opening the kit 886. The customer or user may read the second set of instructions 890 about how to use and recover the image acquisition device. The customer or user may use the image acquisition device as instructed. The customer or user may read the first set of instructions 889 to return the used image acquisition device to the analysis facility in the pre-addressed return mailing device. The customer or user may place the used image acquisition device in the pre-addressed return mailing device and seal the image acquisition device within the pre-addressed return mailing device 880. The customer or user may then mail the return mailing device having the used image acquisition device sealed therein to the image analysis facility via a post office or other common carrier.

Commonly the image analysis facility may analyze the images, as previously described. However, the kit has utility that is not limited to returning the used image acquisition device to the facility to have the images analyzed. As one example, the pre-addressed return mailing device may instead optionally be used to return the used image acquisition device to the facility to have a backup of the images acquired by the image acquisition device stored or archived, whether or not analysis of the images is performed. As one example, the used image acquisition device may be returned to the facility to have tests or repairs made to the image acquisition device, whether or not analysis of the images is performed. Accordingly, the utility of the kit is not limited to only analysis of images.

In one or more embodiments, a used image acquisition device having images stored in an internal memory thereof may be mailed to an image analysis facility. In one or more embodiments, a person who has used the image acquisition device, or a person of whom the images were obtained, may mail the image acquisition device to the image analysis facility.

Figure 9:
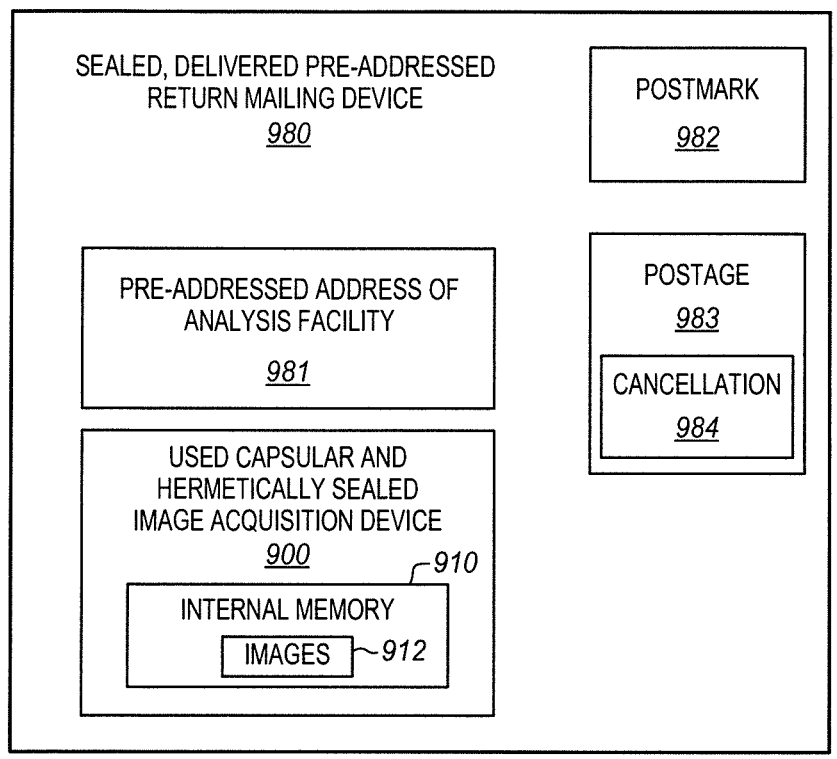
FIG. 9 is a block diagram of an example embodiment of a sealed, delivered optionally pre-addressed return mailing device having a used image acquisition device sealed therein.

FIG. 9 is a block diagram of an example embodiment of a sealed, delivered optionally pre-addressed return envelope, package, or other mailing device 980 having a used capsular and hermetically sealed image acquisition device 900 sealed therein. The used image acquisition device has images 912 stored on an internal memory 910.

As shown, in one or more embodiments, the mailing device may have an address 981 of an image analysis facility. In one or more embodiments, the address of the image analysis facility may be pre-addressed on the mailing device. The address may be located on an exterior of the mailing device at a location predetermined to correspond to the addressee.

As shown, in one or more embodiments, the mailing device may also have a postmark 982, postage 983, and a cancellation 984 of the postage, on an outer surface thereof. The postmark and the cancellation may be as previously described.

To further illustrate certain concepts, consider embodiments applicable to capsule endoscopes.

Current capsule endoscopy procedures tend to be expensive, which significantly limits their widespread use. This is particularly true in the developing world, where the total cost of the procedure may represent a significant fraction of per capita income. As a result, large numbers of people around the world are not able to benefit from capsule endoscopy. Reducing the total cost of performing a capsule endoscopy procedure may help to allow more people around the world to use and benefit from capsule endoscopy. As previously mentioned, this may help to promote early detection and treatment, thereby hopefully increasing patient survival.

In one or more embodiments, an image acquisition device as disclosed herein may be a capsule endoscope. In such embodiments, a user or customer may be a patient who is to use the capsule endoscope. The capsule endoscope may be used to analyze at least a portion of the gastrointestinal tract. The images acquired by the capsule endoscope may be analyzed to detect or identify signs of cancer, other diseases, or other disorders of the gastrointestinal tract, or other diagnostic features of interest.

As used herein, a "capsule endoscope" is to be interpreted broadly as a device that is capable of being swallowed by a human or other patient and that is capable of obtaining an image of an inside of the human or other patient. For example, the housing may have a size and a shape that are capable of being swallowed. The term "capsule" in "capsule endoscope" does not imply a cylindrical or any other particular shape. Various different round, rounded, generally pill-like, generally capsular, and other shapes conventionally used for medicinal capsules and pills, or otherwise capable of being swallowed, are suitable.

Initially, the patient may receive the capsule endoscope having the internal memory, at block 1094. In one or more embodiments, the patient may receive the capsule endoscope without a visit to a physician's office, hospital, or clinic, at least for the purpose only of receiving the capsule endoscope, and without the associated fee typically charged for such a visit. The avoidance of this fee may help to reduce the overall cost of the procedure. This may also help to avoid the inconvenience of having to make and attend the appointment.

In one or more embodiments, the patient may receive the capsule endoscope through the mail and/or from a common carrier. For example, the patient may receive the capsule endoscope in a sealed, delivered mailing device similar to the one shown in FIG. 7. In one or more embodiments, the mailing device may be addressed to an address of the patient, such as, for example, an address of the patient's home, residence, or place of work.

In one or more embodiments, the capsule endoscope may be part of a capsule endoscope kit. For example, the kit may be similar to the one shown in FIG. 8. Examples of other components that may optionally be included in the kit include, but are not limited to, one or more bowel prep compositions (e.g., laxatives and bowel irrigation compositions), gloves, hand sanitizer, a net or other device to catch or restrain the image acquisition device during excretion, charger to charge endoscope prior to use, etc.

Referring again to the illustration, the patient may use and recover the capsule endoscope, at block 1095. Initially, the patient may activate the capsule endoscope. The patient may then swallow the capsule endoscope. Once swallowed, the capsule endoscope may proceed naturally through the gastrointestinal tract. In one or more embodiments, the capsule endoscope may have a pre-programmed delay after being activated, for example ranging from about one to about five hours, before images are obtained. This may help to avoid the obtaining and storing images of an upper portion of the gastrointestinal tract, which in some cases may not be of interest to the analysis. After a period of time often ranging from about 8 to about 12 hours, the patient may pass or excrete the capsule endoscope. The patient may then recover the capsule endoscope having the images stored therein.

Referring again to the illustration, the patient may provide the used capsule endoscope having the images stored therein to an image analysis facility, at block 1096. In one or more embodiments, the patient may provide the used capsule endoscope to the image analysis facility without a visit to a physician's office, hospital, or clinic, and without the associated fee typically charged for such a visit. The avoidance of this fee may help to reduce the overall cost of the procedure. This may also help to avoid the inconvenience of having to make and attend the appointment.

In one or more embodiments, the patient may provide the used capsule endoscope having the images stored therein to the image analysis facility through the mail and/or a common carrier. In one or more embodiments, the patient may mail or send the used capsule endoscope to the image analysis facility in a mailing device that has been pre-addressed with an address of the image analysis facility. For example, the pre-addressed mailing device may be similar to the ones shown in FIG. 8 or 9.

FIG. 11 is a block flow diagram of an example embodiment of a method 1130 that an image analysis facility may perform in conjunction with a capsule endoscope having an internal memory to store images acquired by the capsule endoscope. In one or more embodiments, the image analysis facility may represent a special-purpose image analysis facility that specializes in analyzing images to detect signs of disorders of the gastrointestinal tract. In one or more embodiments, the image analysis facility may be separate from, outside of, and/or not part of, a patient receiving a hospital, a patient treating clinic, or a patient treating office of a physician.

Initially, the image analysis facility may receive the capsule endoscope having the images stored in the internal memory thereof, at block 1131. In one or more embodiments, the image analysis facility may receive the used capsule endoscope through the mail and/or from a common carrier. For example, the image analysis facility may receive the used capsule endoscope in a sealed, delivered mailing device similar to the one shown in FIG. 9. In one or more embodiments, the mailing device may be pre-addressed with an address of the image analysis facility. In one or more embodiments, the used capsule endoscope may be received from a patient who used the capsule endoscope.

Images may be recovered or transferred from the internal memory of the capsule endoscope to an external memory or storage that is external to the capsule endoscope, at block 1132. In one or more embodiments, automated capsule endoscope handling and image recovery equipment may be used. This may help to avoid the need for physicians or nurses to dedicate the time to do this.

An image analysis station may be selected from among a plurality of image analysis stations of the image analysis facility to analyze the images, at block 1133. This may be performed substantially as previously described.

The images may be analyzed at the selected image analysis station, at block 1134. In one or more embodiments, the image analysis station may have a processor and an image display device. The processor may be operable to cause the images to be displayed on the image display device.

In one or more embodiments, a technician, instead of a physician, may analyze the images. The technician may specialize in, and have suitable training in, analyzing images to diagnosis or detect cancers, diseases, and other disorders of the gastrointestinal tract. Typically, a physician would analyze the images. There may be anywhere from hundreds, to thousands, or even tens of thousands of images, or more. Often it would otherwise take the physician between about an hour to several hours to analyze all of the images. Since the hourly wages of the technician are typically significantly less than those of the physician, this may help to significantly reduce the overall cost of the procedure.

The analysis of the images may be completed without a physician analyzing from most to all of the images if no abnormalities or diagnostic features potentially indicative of cancer, disease, or other disorders of the gastrointestinal tract are discovered during the analysis of the images by the technician. Alternatively, the technician may alert a physician if abnormalities or diagnostic features potentially indicative of cancer, disease, or other disorders of the gastrointestinal tract are detected or identified. The physician may be the physician of the patient of whom the images were acquired, or a local physician of the image analysis facility. If the physician of the image analysis facility is not able to conclude that the abnormalities are not indicative of cancer, disease, or other disorders of the gastrointestinal tract, or if no such physician of the image analysis facility is available, the physician of the patient may be alerted. The physician of the patient may optionally be provided with a report indicating that the abnormalities or diagnostic features were detected and potentially be provided images showing the abnormalities or diagnostic features. The physician of the patient may then reanalyze the images, and often perform additional testing or investigation. If no such abnormalities are discovered, the patient and the physician of the patient may be notified accordingly.

A particular example embodiment method has been shown and described in conjunction with FIG. 11. In this method, numerous specific details have been set forth in order to provide a thorough understanding of certain inventive aspects. This method of disclosure, however, is not to be interpreted as reflecting an intention that all of these details are required in combination. Rather, inventive aspects lie in different portions of the disclosed method. Accordingly, the scope of the invention is not limited to the particular method described above.

The cost to obtain and analyze the images using the approach shown in FIGS. 10 and 11 may tend to be significantly less than that of traditional capsule endoscopy procedures. Significant reductions in the cost may be achieved by having a technician instead of a physician analyze the images. Other significant reductions may be achieved by eliminating at least one, if not two, visits to the physician's office, hospital, or clinic. In addition, distributing costs for the image analysis stations and other equipment over a greater number of procedures may help to reducing the equipment cost per procedure.

One technical challenge that presents itself when utilizing potentially remote image analysis facilities to analyze images, instead of a patient's personal physician, is how to efficiently and reliably associate a particular endoscope with the particular patient, information associated with the patient, information associated with the analysis, etc. There is an increased potential for incorrectly associating the endoscope with the wrong patient when numerous endoscopes are processed concurrently at the image analysis facility. Another technical challenge is how to efficiently and reliably communicate the information. A further technical challenge is how to efficiently and reliably communicate what level of analysis is to be performed. Yet another technical challenge is how to provide patient privacy.

Figure 12:
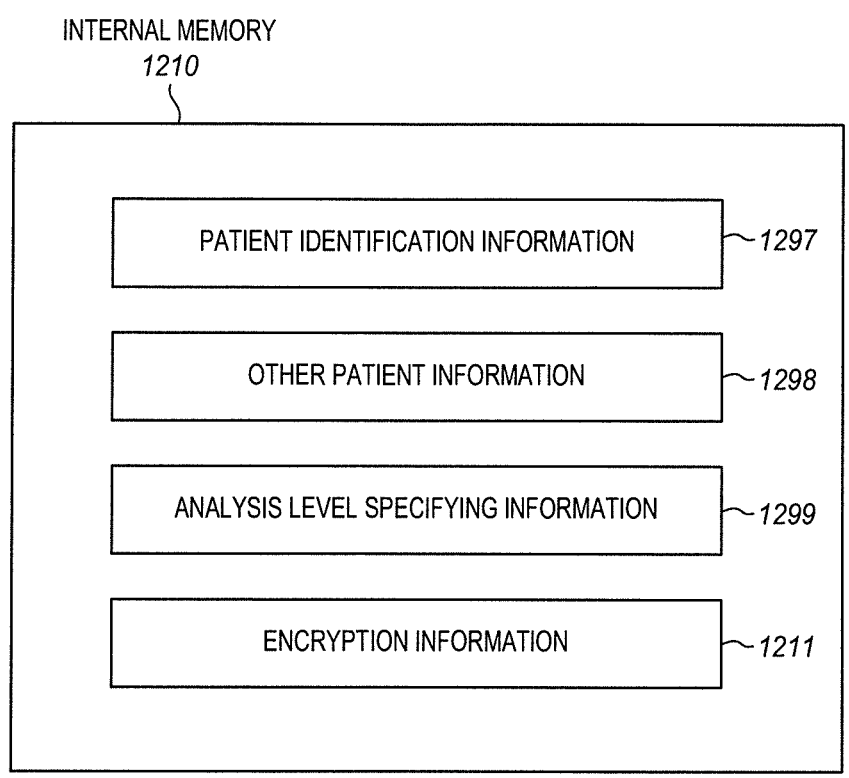
FIG. 12 is a block diagram of an internal memory of a capsule endoscope having various different types of information that may be stored therein according to an example embodiment.

FIG. 12 is a block diagram of an internal memory 1210 of a capsule endoscope having various different types of information that may be stored therein according to an example embodiment. Each of these types of information are optional, not required.

Patient identification information 1297 is one type that may be stored. Example types of patient identification information includes, but is not limited to, patient name, national identification number (e.g., Social Security number), etc.

Other patient information 1298 may also be stored. Examples of such information includes, but is not limited to, patient date of birth, patient age, patient sex, patient weight, patient medical information (e.g., blood type, medical conditions, allergies, medical records), insurance information (e.g., insurance company, insurance contact information, co-pay information, etc.), patient contact information (e.g., patient residence, patient phone number, patient email address, emergency contact person information, etc.), and physician information (e.g., physician name, physician contact information, etc.).

Analysis level specifying information 1299 may also be stored. By way of example, the information may specify a level of analysis, from among a plurality of levels, to be used to analyze the images. The plurality of different levels may include at least a first level of analysis (e.g., a base level), and a second level of analysis (e.g., an enhanced level) that involves more analysis than the first level of analysis. To further illustrate, the first or base level may be a full analysis by one technician, and the second or enhanced level may be a full analysis by a first technician plus an additional redundant full analysis by a second, different technician. This relatively higher second level of analysis may help to provide additional assurance that features of interest are not overlooked. Patients may select the desired level either when requesting the endoscope or when by buying an endoscope preprogrammed with a desired level.

Encryption information 1211 may also be stored. The encryption information, such as, for example, a patient specified password or code, may be used to encrypt or secure and subsequently un-encrypt the images. This may help to provide patient privacy.

Other types of information may also optionally be stored, such as, for example, information specific to the endoscope, specific to the endoscope processing, or that could be useful to analysis stations. In various embodiments, some or all of the aforementioned types of information may be pre-programmed or stored in the capsule endoscope prior to the endoscope being provided to the patient. For example, the patient or the patient's physician may specify the information when requesting the endoscope from a capsule endoscope distributor or the image analysis facility.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention. The scope of the invention is not to be determined by the specific examples provided above but only by the claims below. In other instances, well-known circuits, structures, devices, and operations have been shown in block diagram form or without detail in order to avoid obscuring the understanding of the description.

It will also be appreciated, by one skilled in the art, that modifications may be made to the embodiments disclosed herein, such as, for example, to the sizes, shapes, configurations, forms, functions, and manner of operation, and use, of the components of the embodiments. All equivalent relationships to those illustrated in the drawings and described in the specification are encompassed within embodiments of the invention.

For simplicity and clarity of illustration, elements illustrated in the figures have not necessarily been drawn to scale. Further, where considered appropriate, reference numerals or terminal portions of reference numerals have been repeated among the figures to indicate corresponding or analogous elements, which may optionally have similar characteristics.

Various operations and methods have been described. Some of the methods have been described in a relatively basic form, but operations may optionally be added to and/or removed from the methods. Certain operations of the methods may also often optionally be performed in different order.

One or more embodiments of the invention may be provided as a program product or other article of manufacture that may include a machine-accessible and/or readable medium having stored thereon instructions. The medium may provide instructions, which, if executed by a machine, may result in and/or cause the machine to perform one or more of the operations or methods disclosed herein. Suitable machines include, but are not limited to, computer systems, workstations, image analysis stations, servers, report generation systems, automated handling and data recovery equipment, and a wide variety of other devices with one or more processors, to name just a few examples.

The medium may include, a mechanism that provides, for example stores and/or transmits, information in a form that is accessible by the machine. For example, the medium may optionally include recordable mediums, such as, for example, floppy diskette, optical storage medium, optical disk, CD-ROM, magnetic disk, magneto-optical disk, read only memory (ROM), programmable ROM (PROM), erasable-and-programmable ROM (EPROM), electrically-erasable-and-programmable ROM (EEPROM), random access memory (RAM), static-RAM (SRAM), dynamic-RAM (DRAM), Flash memory, and combinations thereof.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
receiving a capsule endoscope having an internal memory, the internal memory of the capsule endoscope storing images acquired by the capsule endoscope;
transferring the images from the internal memory of the capsule endoscope to an external memory that is external to the capsule endoscope;
selecting an image analysis station from among a plurality of image analysis stations of an analysis facility to analyze the images; and analyzing the images at the selected image analysis station, the selected image analysis station having a processor and an image display device, the processor operable to cause the images to be displayed on the image display device.

2. The method of claim 1, further comprising completing analysis of the images without a physician analyzing from most to all of the images if no abnormalities are discovered during the analysis of the images by the technician.

3. The method of claim 1, further comprising:
detecting an abnormality in an image during the analysis of the images; and
alerting a physician of a patient of whom the images were acquired that the abnormality was detected.

4. The method of claim 1, wherein receiving comprises receiving the capsule endoscope through one of mail and a common carrier, and wherein the capsule endoscope is received in a container having an address of a patient of whom the images were acquired.

5. The method of claim 4, further comprising prior to said receiving the capsule endoscope, sending the capsule endoscope through one of mail and a common carrier to an address of a patient of whom the images were acquired.

6. The method of claim 1, wherein receiving comprises receiving the capsule endoscope through one of mail and a common carrier, and wherein the capsule endoscope is received in a container pre-addressed with an address of an analysis facility having the image analysis stations.

7. The method of claim 1, wherein selecting comprises selecting the image analysis station from among at least five different image analysis stations.

8. The method of claim 1, wherein analyzing comprises redundantly analyzing an identical set of images with both the technician at the selected image analysis station and a second, different technician at a second, different image analysis station.

9. The method of claim 1, wherein receiving comprises receiving a capsule endoscope having patient identification information stored therein which identifies a patient of whom the images have been acquired, and further comprising reading the patient identification information.

10. The method of claim 1, wherein receiving comprises receiving a capsule endoscope having analysis level specifying information stored therein, and wherein analyzing the images is performed according to a level of analysis specified by the analysis level specifying information.

11. The method of claim 1, wherein a technician at the image analysis station analyzes the images.

12. A system comprising:
an image recovery and storage system including:
an image recovery device to recover images that are stored in an internal memory of a capsule endoscope; and
a memory coupled with the image recovery device, the memory to store the images that have been recovered from the capsule endoscope; and
an image analysis system coupled with the image recovery and storage system, the image analysis system including:
a plurality of image analysis stations, each of the image analysis stations including a processor and an image display device, the processor to cause images to be displayed on the image display device, at least one of the image analysis stations to analyze the images recovered from the capsule endoscope and stored in the memory.

13. The system of claim 12, within a special-purpose facility that is not one of a hospital, a patient treating clinic, or a patient treating office of a physician, and that specializes in analyzing images for disorders of the gastrointestinal tract.

14. The system of claim 12, wherein the plurality of image analysis stations comprise at least five different image analysis stations.

15. The system of claim 14, wherein the plurality of image analysis stations comprise at least ten different image analysis stations.

16. The system of claim 12, wherein the image analysis system comprises a selection module coupled with the image analysis stations, the selection module to select the at least one image analysis station to analyze the images.

17. The system of claim 12, further comprising a redundancy module to cause at least two image analysis stations to redundantly analyze a same set of images.

18. The system of claim 12, further comprising a quality control module to provide test images having known correct analysis results to an image analysis station, to receive actual analysis results for the test images from the image analysis station, and to monitor errors based on a comparison of the known correct analysis results with the actual analysis results.

19. The system of claim 12, wherein the image recovery and storage system is to recover analysis level specifying information from the capsule endoscope, the analysis level specifying information specifying a level of analysis to be used to analyze the images, and wherein the image analysis system is to analyze the images according to the specified level of analysis.

20. The system of claim 12, wherein the image analysis system comprises a pre-analysis module to analyze the images prior to the at least one image analysis station analyzing the images, the pre-analysis module to analyze the images for features of interest.

21. The system of claim 12, wherein the image recovery device comprises a probe to contact the capsule endoscope to recover the images.

22. The system of claim 12, wherein the image recovery device comprises a capsule endoscope holder and orientation device, the capsule endoscope holder and orientation device to hold the capsule endoscope and orient the capsule endoscope relative to the image recovery device for the image recovery.

23. The system of claim 12, wherein the image recovery and storage system comprises automated capsule endoscope handling equipment.

24. The system of claim 12, further comprising a report generation system coupled with the image analysis system, the report generation system to generate a report based on the analysis of the images.

25. The system of claim 24, wherein the report generation system comprises a color image generation device to generate a physical color image of an image having a feature of interest to the analysis.

26. An image analysis system comprising:
an image recovery and storage system including:
an image recovery device to recover images that are stored in an internal memory of an encapsulated image acquisition device; and
a memory coupled with the image recovery device, the memory to store the images that have been recovered from the encapsulated image acquisition device; and
an image analysis system coupled with the image recovery and storage system, the image analysis system including:
a plurality of image analysis stations, each of the image analysis stations including a processor and an image display device, the processor to cause images to be displayed on the image display device, at least one of the image analysis stations to analyze the images recovered from the encapsulated image acquisition device and stored in the memory.

27. The image analysis system of claim 26, within a special-purpose analysis facility that specializes in analyzing images for particular types of features of interest.

28. The image analysis system of claim 26, wherein the plurality of age analysis stations comprise at least five different image analysis stations.

29. The image analysis system of claim 28, wherein the plurality of image analysis stations comprise at least ten different image analysis stations.

30. The image analysis system of claim 26, wherein the image analysis system comprises a selection module coupled with the image analysis stations, the selection module to select the at least one image analysis station to analyze the images.

31. The image analysis system of claim 26, further comprising a redundancy module to cause at least two image analysis stations to redundantly analyze a same set of images.

32. The image analysis system of claim 26, further comprising a quality control module to provide test images having known correct analysis results to an image analysis station, to receive actual analysis results for the test images from the image analysis station, and to monitor errors based on a comparison of the known correct analysis results with the actual analysis results.

33. The image analysis system of claim 26, wherein the image recovery and storage system is to recover analysis level specifying information from the encapsulated image acquisition device, the analysis level specifying information specifying a level of analysis to be used to analyze the images, and wherein the image analysis system is to analyze the images according to the specified level of analysis.

34. The image analysis system of claim 26, wherein the image analysis system comprises a pre-analysis module to analyze the images prior to the at least one image analysis station analyzing the images, the pre-analysis module to analyze the images for features of interest.

35. The image analysis system of claim 26, wherein the image recovery device comprises a probe to contact the encapsulated image acquisition device to recover the images.

36. The image analysis system of claim 26, wherein the image recovery device comprises a encapsulated image acquisition device holder and orientation device, the encapsulated image acquisition device holder and orientation device to hold the encapsulated image acquisition device and orient the encapsulated image acquisition device relative to the image recovery device for the image recovery.

37. The image analysis system of claim 26, wherein the image recovery and storage system comprises automated encapsulated image acquisition device handling equipment.

38. The image analysis system of claim 26, further comprising a report generation system coupled with the image analysis system, the report generation system to generate a report based on the analysis of the images.

39. The image analysis system of claim 38, wherein the report generation system comprises a color image generation device to generate a physical color image of an image having a feature of interest to the analysis.

40. A method of analyzing images comprising:
receiving an encapsulated image acquisition device having an internal memory, the internal memory of the encapsulated image acquisition device storing images acquired by the encapsulated image acquisition device;
transferring the images from the internal memory of the encapsulated image acquisition device to an external memory that is external to the encapsulated image acquisition device;
selecting an image analysis station from among a plurality of image analysis stations to analyze the images; and
analyzing the images with the selected image analysis station, the selected image analysis station having a processor and an image display device, the processor operable to cause the images to be displayed on the image display device.

41. The method of analyzing images of claim 40, wherein analyzing comprises analyzing the images to detect a feature of interest in the images.

42. The method of analyzing images of claim 41 wherein analyzing to detect the feature of interest comprises analyzing the images to detect an abnormality in the images.

43. The method of analyzing images of claim 40, further comprising generating a report indicating whether or not a feature of interest was detected during the analysis.

44. The method of analyzing images of claim 40, further comprising:
detecting a feature of interest in an image;
generating a physical copy of the image having the feature of interest;
generating a report that indicates that the feature of interest was detected; and
providing the report and the physical copy of the image having the feature of interest.

45. The method of analyzing images of claim 40, wherein receiving comprises receiving the encapsulated image acquisition device from a person who used the encapsulated image acquisition device.

46. The method of analyzing images of claim 40, wherein receiving comprises receiving the encapsulated image acquisition device through one of mail and from a common carrier, and wherein the encapsulated image acquisition device is received in a container that is pre-addressed with an address of an analysis facility having the image analysis stations.

47. The method of analyzing images of claim 40, wherein selecting comprises selecting the image analysis station from among at least five different image analysis stations, and wherein each of the at least five image analysis stations has a processor and an image display device to display images to a corresponding technician.

48. The method of analyzing images of claim 40, wherein analyzing comprises analyzing a sequence of images of an inner surface of a conduit acquired by the encapsulated image acquisition device as the encapsulated image acquisition device has moved through the conduit.

49. The method of analyzing images of claim 40, wherein analyzing comprises analyzing thousands of images transferred from the internal memory of the encapsulated image acquisition device.

50. The method of analyzing images of claim 40, wherein analyzing comprises redundantly analyzing an identical set of ages with both a first image analysis station and a second image analysis station.

51. The method of analyzing images of claim 40, wherein receiving comprises receiving an encapsulated image acquisition device having person identification information stored therein to identify a person who is to use the encapsulated image acquisition device, and further comprising reading the person identification information by physically contacting a data output port of the encapsulated image acquisition device with a conductor.

52. The method of analyzing images of claim 40, wherein receiving comprises receiving an encapsulated image acquisition device having analysis level specifying information stored therein, and further comprising reading the analysis level specifying information by physically contacting a data output port of the encapsulated image acquisition device with a conductor, and wherein analyzing the images is performed according to a level specified by the analysis level specifying information.

53. The method of analyzing images of claim 40, wherein transferring comprises holding and orienting a data output port of the encapsulated image acquisition device relative to a conductor with a holder and orientation device and contacting the conductor with the data output port of the encapsulated image acquisition device.

* * * * *